United States Patent
Duckworth et al.

(10) Patent No.: US 6,274,380 B1
(45) Date of Patent: Aug. 14, 2001

(54) CACNGLIKE3 POLYNUCLEOTIDES AND EXPRESSION SYSTEMS

(75) Inventors: David Malcolm Duckworth, Bishop's Stortford; Philip David Hayes, Cambridge, both of (GB)

(73) Assignee: SmithKline Beecham PLC, Brentford (GB)

(*) Notice: Subject to any disclaimer, the term of this patent is extended or adjusted under 35 U.S.C. 154(b) by 0 days.

(21) Appl. No.: 09/392,014

(22) Filed: Sep. 8, 1999

(30) Foreign Application Priority Data

Sep. 8, 1998 (GB) .................................... 9819592

(51) Int. Cl.$^7$ ........................... C12N 15/63; C12N 15/00; C12N 5/00; C07H 21/04
(52) U.S. Cl. ................ 435/455; 435/69.1; 435/320.1; 435/325; 435/252.3; 435/254.11; 435/471; 536/23.5; 935/3; 935/6; 935/22; 935/55; 935/66
(58) Field of Search ................ 435/691, 320.1, 435/325, 361, 252.3, 254.11, 440, 455, 465, 471; 536/23.1, 23.5; 935/1, 9, 11, 22, 66, 3, 6, 55

(56) References Cited

FOREIGN PATENT DOCUMENTS

93/13077 * 9/1991 (WO) .

OTHER PUBLICATIONS

Rudinger et al, "Peptide Hormones", ed. Parsons, J.A., University Park Press, Baltimore pp. 1–7, 1976.*
Burgess et al., The Journal of Cell Biology, 111:2129–2138, 1990.*
Lazar et al., The Journal of Cell Biology, 8(3):1247–1252, 1988.*
Jobling et al., Mol. Microbiol., 5(7)1755–1767, 1991.*
Wells et al, Journal of Leukocyle Biology 61:545–550, 1997.*
Gerhold et al, Bio Essays, 18(12):973–981, 1996.*
Russell et al, J. Mol. Biol. 244:332–350, 1994.*
Marra et al, GenBank Accession No. W85386, Sep. 12, 1996.*
Letts, et al. "The mouse stargazer gene encodes a neuronal Ca2+–channel γ subunit", Nature Genetics, vol. 19 (8 pages) 340–347 (1998).
GenBank Accession No. 970202; NCI–CGAP, May 21, 1998.
GenBank Accession No. AC005544, Birren B. et al, Sep. 3, 1998.

* cited by examiner

Primary Examiner—Patricia A. Duffy
(74) Attorney, Agent, or Firm—William T. Han; Ratner & Prestia; William T. King

(57) ABSTRACT

CACNGLIKE3 polypeptides and polynucleotides and methods for producing such polypeptides by recombinant techniques are disclosed. Also disclosed are methods for utilizing CACNGLIKE3 are calcium ion channel family members and CACNGLIKE3 polynucleotides encode for these calcium ion family proteins. Polynucleotides comprising the nucleotide sequences of the present invention provide means for production and manipulation of the CACNGLIKE3 polypeptides. The present invention also provides for the use of CACNGLIKE3 polynucleotides in recombinant expression systems.

9 Claims, No Drawings

CACNGLIKE3 POLYNUCLEOTIDES AND EXPRESSION SYSTEMS

FIELD OF THE INVENTION

This invention relates to newly identified polypeptides and polynucleotides encoding such polypeptides, to their use in diagnosis and in identifying compounds that may be agonists, antagonists that are potentially useful in therapy, and to production of such polypeptides and polynucleotides.

BACKGROUND OF THE INVENTION

The drug discovery process is currently undergoing a fundamental revolution as it embraces "functional genomics", that is, high throughput genome- or gene-based biology. This approach as a means to identify genes and gene products as therapeutic targets is rapidly superceding earlier approaches based on "positional cloning." A phenotype, that is a biological function or genetic disease, would be identified and this would then be tracked back to the responsible gene, based on its genetic map position.

Functional genomics relies heavily on high-throughput DNA sequencing technologies and the various tools of bioinformatics to identify gene sequences of potential interest from the many molecular biology databases now available. There is a continuing need to identify and characterize further genes and their related polypeptides/proteins, as targets for drug discovery.

SUMMARY OF THE INVENTION

The present invention relates to CACNGLIKE3, in particular CACNGLIKE3 polypeptides and CACNGLIKE3 polynucleotides, recombinant materials and methods for their production. Such polypeptides and polynucleotides are of interest in relation to methods of treatment of certain diseases, including, but not limited to, neurological disorders, epilepsies, stroke, head trauma, migraine, affective disorders including depression and anxiety, schizophrenia, neurodegenerative disorders including Alzheimer's disease, cognitive disorders, types of pain and cancer, hereinafter referred to as "diseases of the invention". In a further aspect, the invention relates to methods for identifying agonists and antagonists (e.g., inhibitors) using the materials provided by the invention, and treating conditions associated with CACNGLIKE3 imbalance with the identified compounds. In a still further aspect, the invention relates to diagnostic assays for detecting diseases associated with inappropriate CACNGLIKE3 activity or levels.

DESCRIPTION OF THE INVENTION

In a first aspect, the present invention relates to CACNGLIKE3 polypeptides. Such polypeptides include:
(a) an isolated polypeptide encoded by a polynucleotide comprising the sequence of SEQ ID NO:1;
(b) an isolated polypeptide comprising a polypeptide sequence having at least 95%, 96%, 97%, 98%, or 99% identity to the polypeptide sequence of SEQ ID NO:2;
(c) an isolated polypeptide comprising the polypeptide sequence of SEQ ID NO:2;
(d) an isolated polypeptide having at least 95%, 96%, 97%, 98%, or 99% identity to the polypeptide sequence of SEQ ID NO:2;
(e) the polypeptide sequence of SEQ ID NO:2; and
(f) an isolated polypeptide having or comprising a polypeptide sequence that has an Identity Index of 0.95, 0.96, 0.97, 0.98, or 0.99 compared to the polypeptide sequence of SEQ ID NO:2;
(g) fragments and variants of such polypeptides in (a) to (f).

Polypeptides of the present invention are believed to be members of the calcium ion channel family of polypeptides. They are therefore of interest because of the variety of biological functions that are regulated by them. Voltage-gated calcium channels in particular, are a diverse family of proteins that control calcium entry through a plasma membrane, and are involved in presynaptic neurotransmitter release, intracellular signalling pathways and gene expression. The channels are composed of an alpha1 subunit that serves as the membrane pore and voltage sensor, and several modulatory auxiliary subunits, alpha2-delta and beta. The presence of a gamma subunit is associated with skeletal muscle calcium channels and more recently with brain channels in mice where it is associated with a seizure phenotype, perhaps caused by altered calcium entry into cells (V. A. Letts et al., Nature Genetics 19: 340–347, 1998).

The biological properties of the CACNGLIKE3 are hereinafter referred to as "biological activity of CACNGLIKE3" or "CACNGLIKE3 activity." Preferably, a polypeptide of the present invention exhibits at least one biological activity of CACNGLIKE3.

Polypeptides of the present invention also include variants of the aforementioned polypeptides, including all allelic forms and splice variants. Such polypeptides vary from the reference polypeptide by insertions, deletions, and substitutions that may be conservative or non-conservative, or any combination thereof. Particularly preferred variants are those in which several, for instance from 50 to 30, from 30 to 20, from 20 to 10, from 10 to 5, from 5 to 3, from 3 to 2, from 2 to 1 or 1 amino acids are inserted, substituted, or deleted, in any combination.

Preferred fragments of polypeptides of the present invention include an isolated polypeptide comprising an amino acid sequence having at least 30, 50 or 100 contiguous amino acids from the amino acid sequence of SEQ ID NO:2, or an isolated polypeptide comprising an amino acid sequence having at least 30, 50 or 100 contiguous amino acids truncated or deleted from the amino acid sequence of SEQ ID NO:2. Preferred fragments are biologically active fragments that mediate the biological activity of CACNGLIKE3, including those with a similar activity or an improved activity, or with a decreased undesirable activity. Also preferred are those fragments that are antigenic or immunogenic in an animal, especially in a human.

Fragments of the polypeptides of the invention may be employed for producing the corresponding full-length polypeptide by peptide synthesis; therefore, these variants may be employed as intermediates for producing the full-length polypeptides of the invention. The polypeptides of the present invention may be in the form of the "mature" protein or may be a part of a larger protein such as a precursor or a fusion protein. It is often advantageous to include an additional amino acid sequence that contains secretory or leader sequences, pro-sequences, sequences that aid in purification, for instance multiple histidine residues, or an additional sequence for stability during recombinant production.

Polypeptides of the present invention can be prepared in any suitable manner, for instance by isolation form naturally occurring sources, from genetically engineered host cells comprising expression systems (vide infra) or by chemical synthesis, using for instance automated peptide synthesizers, or a combination of such methods. Means for preparing such polypeptides are well understood in the art.

In a further aspect, the present invention relates to CACNGLIKE3 polynucleotides. Such polynucleotides include:
(a) an isolated polynucleotide comprising a polynucleotide sequence having at least 95%, 96%, 97%, 98%, or 99% identity to the polynucleotide sequence of SEQ ID NO:1;
(b) an isolated polynucleotide comprising the polynucleotide of SEQ ID NO:1;

(c) an isolated polynucleotide having at least 95%, 96%, 97%, 98%, or 99% identity to the polynucleotide of SEQ ID NO:1;
(d) the isolated polynucleotide of SEQ ID NO:1;
(e) an isolated polynucleotide comprising a polynucleotide sequence encoding a polypeptide sequence having at least 95%, 96%, 97%, 98%, or 99% identity to the polypeptide sequence of SEQ ID NO:2;
(f) an isolated polynucleotide comprising a polynucleotide sequence encoding the polypeptide of SEQ ID NO:2;
(g) an isolated polynucleotide having a polynucleotide sequence encoding a polypeptide sequence having at least 95%, 96%, 97%, 98%, or 99% identity to the polypeptide sequence of SEQ ID NO:2;
(h) an isolated polynucleotide encoding the polypeptide of SEQ ID NO:2;
(i) an isolated polynucleotide having or comprising a polynucleotide sequence that has an Identity Index of 0.95, 0.96, 0.97, 0.98, or 0.99 compared to the polynucleotide sequence of SEQ ID NO:1;
(j) an isolated polynucleotide having or comprising a polynucleotide sequence encoding a polypeptide sequence that has an Identity Index of 0.95, 0.96, 0.97, 0.98, or 0.99 compared to the polypeptide sequence of SEQ ID NO:2; and polynucleotides that are fragments and variants of the above mentioned polynucleotides or that are complementary to above mentioned polynucleotides, over the entire length thereof.

Preferred fragments of polynucleotides of the present invention include an isolated polynucleotide comprising an nucleotide sequence having at least 15, 30, 50 or 100 contiguous nucleotides from the sequence of SEQ ID NO:1, or an isolated polynucleotide comprising an sequence having at least 30, 50 or 100 contiguous nucleotides truncated or deleted from the sequence of SEQ ID NO:1.

Preferred variants of polynucleotides of the present invention include splice variants, allelic variants, and polymorphisms, including polynucleotides having one or more single nucleotide polymorphisms (SNPs).

Polynucleotides of the present invention also include polynucleotides encoding polypeptide variants that comprise the amino acid sequence of SEQ ID NO:2 and in which several, for instance from 50 to 30, from 30 to 20, from 20 to 10, from 10 to 5, from 5 to 3, from 3 to 2, from 2 to 1 or 1 amino acid residues are substituted, deleted or added, in any combination.

In a further aspect, the present invention provides polynucleotides that are RNA transcripts of the DNA sequences of the present invention. Accordingly, there is provided an RNA polynucleotide that:
(a) comprises an RNA transcript of the DNA sequence encoding the polypeptide of SEQ ID NO:2;
(b) is the RNA transcript of the DNA sequence encoding the polypeptide of SEQ ID NO:2;
(c) comprises an RNA transcript of the DNA sequence of SEQ ID NO:1; or
(d) is the RNA transcript of the DNA sequence of SEQ ID NO: 1;
and RNA polynucleotides that are complementary thereto.

The polynucleotide sequence of SEQ ID NO:1 shows homology with mouse voltage-gated calcium channel gamma-2 subunit, Cacng2 (V. A. Letts et al., Nature Genetics 19: 340–347, 1998). The polynucleotide sequence of SEQ ID NO:1 is a cDNA sequence that encodes the polypeptide of SEQ ID NO:2. The polynucleotide sequence encoding the polypeptide of SEQ ID NO:2 may be identical to the polypeptide encoding sequence of SEQ ID NO:1 or it may be a sequence other than SEQ ID NO:1, which, as a result of the redundancy (degeneracy) of the genetic code, also encodes the polypeptide of SEQ ID NO:2. The polypeptide of the SEQ ID NO:2 is related to other proteins of the calcium ion channel family, having homology and/or structural similarity with mouse voltage-gated calcium channel gamma-2 subunit, Cacng2 (V. A. Letts et al., Nature Genetics 19: 340–347, 1998).

Preferred polypeptides and polynucleotides of the present invention are expected to have, inter alia, similar biological functions/properties to their homologous polypeptides and polynucleotides. Furthermore, preferred polypeptides and polynucleotides of the present invention have at least one CACNGLIKE3 activity.

The present invention also relates to partial or other polynucleotide and polypeptide sequences which were first identified prior to the determination of the corresponding full length sequences of SEQ ID NO:1 and SEQ ID NO:2.

Accordingly, in a further aspect, the present invention provides for an isolated polynucleotide which:
(a) comprises a nucleotide sequence which has at least 95% identity, preferably at least 97–99% identity to SEQ ID NO:3 over the entire length of SEQ ID NO:3;
(b) has a nucleotide sequence which has at least 95% identity, preferably at least 97–99% identity, to SEQ ID NO:3 over the entire length of SEQ ID NO:3;
(c) comprises the polynucleotide of SEQ ID NO:3; or
(d) has a nucleotide sequence encoding a polypeptide which has at least 95% identity, even more preferably at least 97–99% identity, to the amino acid sequence of SEQ ID NO:4, over the entire length of SEQ ID NO:4;
as well as the polynucleotide of SEQ ID NO:3.

The present invention further provides for a polypeptide which:
(a) comprises an amino acid sequence which has at least 95% identity, preferably at least 97–99% identity, to that of SEQ ID NO:4 over the entire length of SEQ ID NO:4;
(b) has an amino acid sequence which is at least 95% identity, preferably at least 97–99% identity, to the amino acid sequence of SEQ ID NO:4 over the entire length of SEQ ID NO:4;
(c) comprises the amino acid of SEQ ID NO:4; and
(d) is the polypeptide of SEQ ID NO:4;
as well as polypeptides encoded by a polynucleotide comprising the sequence contained in SEQ ID NO:3.

The nucleotide sequence of SEQ ID NO:3 and the peptide sequence encoded thereby are derived from EST (Expressed Sequence Tag) sequences. It is recognised by those skilled in the art that there will inevitably be some nucleotide sequence reading errors in EST sequences (see Adams, M. D. et al, Nature 377 (supp) 3, 1995). Accordingly, the nucleotide sequence of SEQ ID NO:3 and the peptide sequence encoded therefrom are therefore subject to the same inherent limitations in sequence accuracy. Furthermore, the peptide sequence encoded by SEQ ID NO:3 comprises a region of identity or close homology and/or close structural similarity (for example a conservative amino acid difference) with the closest homologous or structurally similar protein.

Polynucleotides of the present invention may be obtained using standard cloning and screening techniques from a cDNA library derived from mRNA in cells of a human brain, oligodendroglioma and kidney,, (see for instance, Sambrook et al., Molecular Cloning: A Laboratory Manual, 2nd Ed., Cold Spring Harbor Laboratory Press, Cold Spring Harbor, N.Y. (1989)). Polynucleotides of the invention can also be obtained from natural sources such as genomic DNA libraries or can be synthesized using well known and commercially available techniques.

When polynucleotides of the present invention are used for the recombinant production of polypeptides of the present invention, the polynucleotide may include the coding sequence for the mature polypeptide, by itself, or the coding sequence for the mature polypeptide in reading frame with other coding sequences, such as those encoding a leader or secretory sequence, a pre-, or pro- or prepro- protein sequence, or other fusion peptide portions. For example, a marker sequence that facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., Proc Natl Acad Sci USA (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Polynucleotides that are identical, or have sufficient identity to a polynucleotide sequence of SEQ ID NO:1, may be used as hybridization probes for cDNA and genomic DNA or as primers for a nucleic acid amplification reaction (for instance, PCR). Such probes and primers may be used to isolate full-length cDNAs and genomic clones encoding polypeptides of the present invention and to isolate cDNA and genomic clones of other genes (including genes encoding paralogs from human sources and orthologs and paralogs from species other than human) that have a high sequence similarity to SEQ ID NO:1, typically at least 95% identity. Preferred probes and primers will generally comprise at least 15 nucleotides, preferably, at least 30 nucleotides and may have at least 50, if not at least 100 nucleotides. Particularly preferred probes will have between 30 and 50 nucleotides. Particularly preferred primers will have between 20 and 25 nucleotides.

A polynucleotide encoding a polypeptide of the present invention, including homologs from species other than human, may be obtained by a process comprising the steps of screening a library under stringent hybridization conditions with a labeled probe having the sequence of SEQ ID NO:1 or a fragment thereof, preferably of at least 15 nucleotides; and isolating full-length cDNA and genomic clones containing said polynucleotide sequence. Such hybridization techniques are well known to the skilled artisan. Preferred stringent hybridization conditions include overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 microgram/ml denatured, sheared salmon sperm DNA; followed by washing the filters in 0.1×SSC at about 65° C. Thus the present invention also includes isolated polynucleotides, preferably with a nucleotide sequence of at least 100, obtained by screening a library under stringent hybridization conditions with a labeled probe having the sequence of SEQ ID NO:1 or a fragment thereof, preferably of at least 15 nucleotides.

The skilled artisan will appreciate that, in many cases, an isolated cDNA sequence will be incomplete, in that the region coding for the polypeptide does not extend all the way through to the 5' terminus. This is a consequence of reverse transcriptase, an enzyme with inherently low "processivity" (a measure of the ability of the enzyme to remain attached to the template during the polymerization reaction), failing to complete a DNA copy of the mRNA template during first strand cDNA synthesis.

There are several methods available and well known to those skilled in the art to obtain full-length cDNAs, or extend short cDNAs, for example those based on the method of Rapid Amplification of cDNA ends (RACE) (see, for example, Frohman et al., Proc Nat Acad Sci USA 85, 8998–9002, 1988). Recent modifications of the technique, exemplified by the Marathon (trade mark) technology (Clontech Laboratories Inc.) for example, have significantly simplified the search for longer cDNAs. In the Marathon (trade mark) technology, cDNAs have been prepared from mRNA extracted from a chosen tissue and an 'adaptor' sequence ligated onto each end. Nucleic acid amplification (PCR) is then carried out to amplify the "missing" 5' end of the cDNA using a combination of gene specific and adaptor specific oligonucleotide primers. The PCR reaction is then repeated using 'nested' primers, that is, primers designed to anneal within the amplified product (typically an adaptor specific primer that anneals further 3' in the adaptor sequence and a gene specific primer that anneals further 5' in the known gene sequence). The products of this reaction can then be analyzed by DNA sequencing and a full-length cDNA constructed either by joining the product directly to the existing cDNA to give a complete sequence, or carrying out a separate full-length PCR using the new sequence information for the design of the 5' primer.

Recombinant polypeptides of the present invention may be prepared by processes well known in the art from genetically engineered host cells comprising expression systems. Accordingly, in a further aspect, the present invention relates to expression systems comprising a polynucleotide or polynucleotides of the present invention, to host cells which are genetically engineered with such expression systems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Polynucleotides may be introduced into host cells by methods described in many standard laboratory manuals, such as Davis et al., Basic Methods in Molecular Biology (1986) and Sambrook et al.(ibid). Preferred methods of introducing polynucleotides into host cells include, for instance, calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as Streptococci, Staphylococci, *E. coli*, Streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector that is able to maintain, propagate or express a polynucleotide to produce a polypeptide in a host may be used. The appropriate polynucleotide sequence may be inserted into an expression system by any of a variety of well-known and routine techniques, such as, for example, those set forth in Sambrook et al., (ibid). Appropriate secretion signals may be incorporated into the desired polypeptide to allow secretion of the translated protein into the lumen of the endoplasmic reticulum, the periplasmic space or the extracellular environment. These signals may be endogenous to the polypeptide or they may be heterologous signals.

If a polypeptide of the present invention is to be expressed for use in screening assays, it is generally preferred that the polypeptide be produced at the surface of the cell. In this event, the cells may be harvested prior to use in the screening assay. If the polypeptide is secreted into the medium, the medium can be recovered in order to recover and purify the polypeptide. If produced intracellularly, the cells must first be lysed before the polypeptide is recovered.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during intracellular synthesis, isolation and/or purification.

Polynucleotides of the present invention may be used as diagnostic reagents, through detecting mutations in the associated gene. Detection of a mutated form of the gene characterized by the polynucleotide of SEQ ID NO:1 in the cDNA or genomic sequence and which is associated with a dysfunction will provide a diagnostic tool that can add to, or define, a diagnosis of a disease, or susceptibility to a disease, which results from under-expression, over-expression or altered spatial or temporal expression of the gene. Individuals carrying mutations in the gene may be detected at the DNA level by a variety of techniques well known in the art.

Nucleic acids for diagnosis may be obtained from a subject's cells, such as from blood, urine, saliva, tissue biopsy or autopsy material. The genomic DNA may be used directly for detection or it may be amplified enzymatically by using PCR, preferably RT-PCR, or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled CACNGLIKE3 nucleotide sequences. Perfectly matched sequences can be distinguished from mismatched duplexes by RNase digestion or by differences in melting temperatures. DNA sequence difference may also be detected by alterations in the electrophoretic mobility of DNA fragments in gels, with or without denaturing agents, or by direct DNA sequencing (see, for instance, Myers et al., Science (1985) 230:1242). Sequence changes at specific locations may also be revealed by nuclease protection assays, such as RNase and S1 protection or the chemical cleavage method (see Cotton et al., Proc Natl Acad Sci USA (1985) 85: 4397–4401).

An array of oligonucleotides probes comprising CACNG-LIKE3 polynucleotide sequence or fragments thereof can be constructed to conduct efficient screening of e.g., genetic mutations. Such arrays are preferably high density arrays or grids. Array technology methods are well known and have general applicability and can be used to address a variety of questions in molecular genetics including gene expression, genetic linkage, and genetic variability, see, for example, M. Chee et al., Science, 274, 610–613 (1996) and other references cited therein.

Detection of abnormally decreased or increased levels of polypeptide or mRNA expression may also be used for diagnosing or determining susceptibility of a subject to a disease of the invention. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods. Assay techniques that can be used to determine levels of a protein, such as a polypeptide of the present invention, in a sample derived from a host are well-known to those of skill in the art. Such assay methods include radioimmunoassays, competitive-binding assays, Western Blot analysis and ELISA assays.

Thus in another aspect, the present invention relates to a diagnostic kit comprising:

(a) a polynucleotide of the present invention, preferably the nucleotide sequence of SEQ ID NO:1, or a fragment or an RNA transcript thereof;

(b) a nucleotide sequence complementary to that of (a);

(c) a polypeptide of the present invention, preferably the polypeptide of SEQ ID NO:2 or a fragment thereof; or (d) an antibody to a polypeptide of the present invention, preferably to the polypeptide of SEQ ID NO:2.

It will be appreciated that in any such kit, (a), (b), (c) or (d) may comprise a substantial component. Such a kit will be of use in diagnosing a disease or susceptibility to a disease, particularly diseases of the invention, amongst others.

The polynucleotide sequences of the present invention are valuable for chromosome localization studies. The sequence is specifically targeted to, and can hybridize with, a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationship between genes and diseases that have been mapped to the same chromosomal region are then identified through linkage analysis (co-inheritance of physically adjacent genes). Precise human chromosomal localizations for a genomic sequence (gene fragment etc.) can be determined using Radiation Hybrid (RH) Mapping (Walter, M. Spillett, D., Thomas, P., Weissenbach, J., and Goodfellow, P., (1994) A method for constructing radiation hybrid maps of whole genomes, Nature Genetics 7, 22–28). A number of RH panels are available from Research Genetics (Huntsville, Ala., USA) e.g. the GeneBridge4 RH panel (Hum Mol Genet Mar. 5, 1996 (3):339–46 A radiation hybrid map of the human genome. Gyapay G, Schmitt K, Fizames C, Jones H, Vega-Czarny N, Spillett D, Muselet D, Prud'Homme J F, Dib C, Auffray C, Morissette J, Weissenbach J, Goodfellow P N). To determine the chromosomal location of a gene using this panel, 93 PCRs are performed using primers designed from the gene of interest on RH DNAs. Each of these DNAs contains random human genomic fragments maintained in a hamster background (human/hamster hybrid cell lines). These PCRs result in 93 scores indicating the presence or absence of the PCR product of the gene of interest. These scores are compared with scores created using PCR products from genomic sequences of known location. This comparison is conducted at http://www.genome.wi.mit.edu/. The gene of the present invention maps to human chromosome 17q24.3.

The polynucleotide sequences of the present invention are also valuable tools for tissue expression studies. Such studies allow the determination of expression patterns of polynucleotides of the present invention which may give an indication as to the expression patterns of the encoded polypeptides in tissues, by detecting the mRNAs that encode them. The techniques used are well known in the art and include in situ hybridization techniques to clones arrayed on a grid, such as cDNA microarray hybridization (Schena et al, Science, 270, 467–470, 1995 and Shalon et al, Genome Res, 6, 639–645, 1996) and nucleotide amplification techniques such as PCR. A preferred method uses the TAQMAN (Trade mark) technology available from Perkin Elmer. Results from these studies can provide an indication of the normal function of the polypeptide in the organism. In addition, comparative studies of the normal expression pattern of mRNAs with that of mRNAs encoded by an alternative form of the same gene (for example, one having an alteration in polypeptide coding potential or a regulatory mutation) can provide valuable insights into the role of the polypeptides of the present invention, or that of inappropriate expression thereof in disease. Such inappropriate expression may be of a temporal, spatial or simply quantitative nature.

A further aspect of the present invention relates to antibodies. The polypeptides of the invention or their fragments, or cells expressing them, can be used as immunogens to produce antibodies that are immunospecific for polypeptides of the present invention. The term "immunospecific" means that the antibodies have substantially greater affinity for the polypeptides of the invention than their affinity for other related polypeptides in the prior art.

Antibodies generated against polypeptides of the present invention may be obtained by administering the polypeptides or epitope-bearing fragments, or cells to an animal, preferably a non-human animal, using routine protocols. For preparation of monoclonal antibodies, any technique which provides antibodies produced by continuous cell line cultures can be used. Examples include the hybridoma technique (Kohler, G. and Milstein, C., Nature (1975) 256:495–497), the trioma technique, the human B-cell hybridoma technique (Kozbor et al., Immunology Today (1983) 4:72) and the EBV-hybridoma technique (Cole et al., Monoclonal Antibodies and Cancer Therapy, 77–96, Alan R. Liss, Inc., 1985).

Techniques for the production of single chain antibodies, such as those described in U.S. Pat. No. 4,946,778, can also be adapted to produce single chain antibodies to polypeptides of this invention. Also, transgenic mice, or other organisms, including other mammals, may be used to express humanized antibodies.

The above-described antibodies may be employed to isolate or to identify clones expressing the polypeptide or to purify the polypeptides by affinity chromatography. Antibodies against polypeptides of the present invention may also be employed to treat diseases of the invention, amongst others.

Polypeptides and polynucleotides of the present invention may also be used as vaccines. Accordingly, in a further aspect, the present invention relates to a method for inducing an immunological response in a mammal that comprises inoculating the mammal with a polypeptide of the present invention, adequate to produce antibody and/or T cell immune response, including, for example, cytokine-producing T cells or cytotoxic T cells, to protect said animal from disease, whether that disease is already established within the individual or not. An immunological response in a mammal may also be induced by a method comprises delivering a polypeptide of the present invention via a vector directing expression of the polynucleotide and coding for the polypeptide in vivo in order to induce such an immunological response to produce antibody to protect said animal from diseases of the invention. One way of administering the vector is by accelerating it into the desired cells as a coating on particles or otherwise. Such nucleic acid vector may comprise DNA, RNA, a modified nucleic acid, or a DNA/RNA hybrid. For use a vaccine, a polypeptide or a nucleic acid vector will be normally provided as a vaccine formulation (composition). The formulation may further comprise a suitable carrier. Since a polypeptide may be broken down in the stomach, it is preferably administered parenterally (for instance, subcutaneous, intramuscular, intravenous, or intradermal injection). Formulations suitable for parenteral administration include aqueous and non-aqueous sterile injection solutions that may contain anti-oxidants, buffers, bacteriostats and solutes that render the formulation instonic with the blood of the recipient; and aqueous and non-aqueous sterile suspensions that may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Polypeptides of the present invention have one or more biological functions that are of relevance in one or more disease states, in particular the diseases of the invention hereinbefore mentioned. It is therefore useful to identify compounds that stimulate or inhibit the function or level of the polypeptide. Accordingly, in a further aspect, the present invention provides for a method of screening compounds to identify those that stimulate or inhibit the function or level of the polypeptide. Such methods identify agonists or antagonists that may be employed for therapeutic and prophylactic purposes for such diseases of the invention as hereinbefore mentioned. Compounds may be identified from a variety of sources, for example, cells, cell-free preparations, chemical libraries, collections of chemical compounds, and natural product mixtures. Such agonists or antagonists so-identified may be natural or modified substrates, ligands, receptors, enzymes, etc., as the case may be, of the polypeptide; a structural or functional mimetic thereof (see Coligan et al., Current Protocols in Immunology 1(2):Chapter 5 (1991)) or a small molecule. Such small molecules preferably have a molecular weight below 2,000 daltons, more preferably between 300 and 1,000 daltons, and most preferably between 400 and 700 daltons. It is preferred that these small molecules are organic molecules.

The screening method may simply measure the binding of a candidate compound to the polypeptide, or to cells or membranes bearing the polypeptide, or a fusion protein thereof, by means of a label directly or indirectly associated with the candidate compound. Alternatively, the screening method may involve measuring or detecting (qualitatively or quantitatively) the competitive binding of a candidate compound to the polypeptide against a labeled competitor (e.g. agonist or antagonist). Further, these screening methods may test whether the candidate compound results in a signal generated by activation or inhibition of the polypeptide, using detection systems appropriate to the cells bearing the polypeptide. Inhibitors of activation are generally assayed in the presence of a known agonist and the effect on activation by the agonist by the presence of the candidate compound is observed. Further, the screening methods may simply comprise the steps of mixing a candidate compound with a solution containing a polypeptide of the present invention, to form a mixture, measuring a CACNGLIKE3 activity in the mixture, and comparing the CACNGLIKE3 activity of the mixture to a control mixture which contains no candidate compound.

Polypeptides of the present invention may be employed in conventional low capacity screening methods and also in high-throughput screening (HTS) formats. Such HTS formats include not only the well-established use of 96- and, more recently, 384-well micotiter plates but also emerging methods such as the nanowell method described by Schullek et al, Anal Biochem., 246, 20–29, (1997).

Fusion proteins, such as those made from Fc portion and CACNGLIKE3 polypeptide, as hereinbefore described, can also be used for high-throughput screening assays to identify antagonists for the polypeptide of the present invention (see D. Bennett et al., J Mol Recognition, 8:52–58 (1995); and K. Johanson et al., J Biol Chem, 270(16):9459–9471 (1995)).

The polynucleotides, polypeptides and antibodies to the polypeptide of the present invention may also be used to configure screening methods for detecting the effect of added compounds on the production of mRNA and polypeptide in cells. For example, an ELISA assay may be constructed for measuring secreted or cell associated levels of polypeptide using monoclonal and polyclonal antibodies by standard methods known in the art. This can be used to discover agents that may inhibit or enhance the production of polypeptide (also called antagonist or agonist, respectively) from suitably manipulated cells or tissues.

A polypeptide of the present invention may be used to identify membrane bound or soluble receptors, if any, through standard receptor binding techniques known in the art. These include, but are not limited to, ligand binding and crosslinking assays in which the polypeptide is labeled with a radioactive isotope (for instance, $^{125}$I), chemically modified (for instance, biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. These screening methods may also be used to identify agonists and antagonists of the polypeptide that compete with the binding of the polypeptide to its receptors, if any. Standard methods for conducting such assays are well understood in the art.

Examples of antagonists of the polypeptides of the present invention include antibodies or, in some cases, oligonucleotides or proteins that are closely related to the ligands, substrates, receptors, enzymes, etc., as the case may be, of the polypeptide, e.g., a fragment of the ligands, substrates, receptors, enzymes, etc.; or a small molecule that bind to the polypeptide of the present invention but do not elicit a response, so that the activity of the polypeptide is prevented.

Screening methods may also involve the use of transgenic technology and CACNGLIKE3 gene. The art of constructing transgenic animals is well established. For example, the CACNGLIKE3 gene may be introduced through microinjection into the male pronucleus of fertilized oocytes, retroviral transfer into pre- or post-implantation embryos, or injection of genetically modified, such as by electroporation, embryonic stem cells into host blastocysts. Particularly useful transgenic animals are so-called "knock-in" animals in which an animal gene is replaced by the human equivalent within the genome of that animal. Knock-in transgenic animals are useful in the drug discovery process, for target validation, where the compound is specific for the human target. Other useful transgenic animals are so-called "knock-out" animals in which the expression of the animal ortholog of a polypeptide of the present invention and encoded by an endogenous DNA sequence in a cell is partially or completely annulled. The gene knock-out may be targeted to specific cells or tissues, may occur only in certain cells or tissues as a consequence of the limitations of the technology, or may occur in all, or substantially all, cells in the animal. Transgenic animal technology also offers a whole animal expression-cloning system in which introduced genes are expressed to give large amounts of polypeptides of the present invention Screening kits for use in the above described methods form a further aspect of the present invention. Such screening kits comprise:

(a) a polypeptide of the present invention;
(b) a recombinant cell expressing a polypeptide of the present invention;
(c) a cell membrane expressing a polypeptide of the present invention; or
(d) an antibody to a polypeptide of the present invention; which polypeptide is preferably that of SEQ ID NO:2.

It will be appreciated that in any such kit, (a), (b), (c) or (d) may comprise a substantial component.

Glossary

The following definitions are provided to facilitate understanding of certain terms used frequently hereinbefore.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Polynucleotide" generally refers to any polyribonucleotide (RNA) or polydeoxribonucleotide (DNA), which may be unmodified or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any polypeptide comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques that are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross4inking, cyclization, disulfide bond formation, demethylation, formation of covalent cross-links, formation of cystine, formation of pyroglutamate, formylamino, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, Proteins—Structure and Molecular Properties, 2nd Ed., T. E. Creighton, W. H. Freeman and Company, New York, 1993; Wold, F., Post-translational Protein Modifications: Perspectives and Prospects, 1–12, in Post-translational Covalent Modification of Proteins, B. C. Johnson, Ed., Academic Press, New York, 1983; Seifter et al., "Analysis for protein modifications and nonprotein cofactors", Meth Enzymol, 182, 626–646, 1990, and Rattan et al., "Protein Synthesis: Post-translational Modifications and Aging", Ann NY Acad Sci, 663, 48–62, 1992).

"Fragment" of a polypeptide sequence refers to a polypeptide sequence that is shorter than the reference sequence but that retains essentially the same biological function or activity as the reference polypeptide. "Fragment" of a polynucleotide sequence refers to a polynucleotide sequence that is shorter than the reference sequence of SEQ ID NO:1.

"Variant" refers to a polynucleotide or polypeptide that differs from a reference polynucleotide or polypeptide, but retains the essential properties thereof. A typical variant of a polynucleotide differs in nucleotide sequence from the reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from the reference polypeptide. Generally, alterations are limited so that the sequences of the reference polypeptide and the variant are closely similar overall and, in many regions, identical. A variant and reference polypeptide may differ in amino acid sequence by one or more substitutions, insertions, deletions in any combination. A substituted or inserted amino acid residue may or may not be one encoded by the genetic code. Typical conservative substitutions include Gly, Ala; Val, Ile, Leu; Asp, Glu; Asn, Gln; Ser, Thr; Lys, Arg; and Phe and Tyr. A variant of a polynucleotide or polypeptide may be naturally occurring such as an allele, or it may be a variant that is not known to occur naturally. Non-naturally occurring variants of polynucleotides and polypeptides may be made by mutagenesis techniques or by direct synthesis. Also included as variants are polypeptides having one or more post-translational modifications, for instance glycosylation, phosphorylation, methylation, ADP ribosylation and the like. Embodiments include methylation of the N-terminal amino acid, phosphorylations of serines and threonines and modification of C-terminal glycines.

"Allele" refers to one of two or more alternative forms of a gene occurring at a given locus in the genome.

"Polymorphism" refers to a variation in nucleotide sequence (and encoded polypeptide sequence, if relevant) at a given position in the genome within a population.

"Single Nucleotide Polymorphism" (SNP) refers to the occurrence of nucleotide variability at a single nucleotide position in the genome, within a population. An SNP may occur within a gene or within intergenic regions of the genome. SNPs can be assayed using Allele Specific Amplification (ASA). For the process at least 3 primers are required. A common primer is used in reverse complement to the polymorphism being assayed. This common primer can be between 50 and 1500 bps from the polymorphic base. The other two (or more) primers are identical to each other except that the final 3' base wobbles to match one of the two (or more) alleles that make up the polymorphism. Two (or more) PCR reactions are then conducted on sample DNA, each using the common primer and one of the Allele Specific Primers.

"Splice Variant" as used herein refers to cDNA molecules produced from RNA molecules initially transcribed from the same genomic DNA sequence but which have undergone alternative RNA splicing. Alternative RNA splicing occurs when a primary RNA transcript undergoes splicing, generally for the removal of introns, which results in the production of more than one mRNA molecule each of that may encode different amino acid sequences. The term splice variant also refers to the proteins encoded by the above cDNA molecules.

"Identity" reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

"% Identity"— For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

"Similarity" is a further, more sophisticated measure of the relationship between two polypeptide sequences. In general, "similarity" means a comparison between the amino acids of two polypeptide chains, on a residue by residue basis, taking into account not only exact correspondences between a between pairs of residues, one from each of the sequences being compared (as for identity) but also, where there is not an exact correspondence, whether, on an evolutionary basis, one residue is a likely substitute for the other. This likelihood has an associated "score" from which the "% similarity" of the two sequences can then be determined.

Methods for comparing the identity and similarity of two or more sequences are well known in the art. Thus for instance, programs available in the Wisconsin Sequence Analysis Package, version 9.1 (Devereux J et al, Nucleic Acids Res, 12, 387–395, 1984, available from Genetics Computer Group, Madison, Wis., USA), for example the programs BESTFIT and GAP, may be used to determine the % identity between two polynucleotides and the % identity and the % similarity between two polypeptide sequences. BESTFIT uses the "local homology" algorithm of Smith and Waterman (J Mol Biol, 147,195–197, 1981, Advances in Applied Mathematics, 2, 482–489, 1981) and finds the best single region of similarity between two sequences. BEST-FIT is more suited to comparing two polynucleotide or two polypeptide sequences that are dissimilar in length, the program assuming that the shorter sequence represents a portion of the longer. In comparison, GAP aligns two sequences, finding a "maximum similarity" , according to the algorithm of Neddleman and Wunsch (J Mol Biol, 48, 443–453, 1970). GAP is more suited to comparing sequences that are approximately the same length and an alignment is expected over the entire length. Preferably, the parameters "Gap Weight" and "Length Weight" used in each program are 50 and 3, for polynucleotide sequences and 12 and 4 for polypeptide sequences, respectively. Preferably, % identities and similarities are determined when the two sequences being compared are optimally aligned.

Other programs for determining identity and/or similarity between sequences are also known in the art, for instance the BLAST family of programs (Altschul S F et al, J Mol Biol, 215, 403–410, 1990, Altschul S F et al, Nucleic Acids Res., 25:389–3402, 1997, available from the National Center for Biotechnology Information (NCBI), Bethesda, Md., USA and accessible through the home page of the NCBI at www.ncbi.nlm.nih.gov) and FASTA (Pearson W R, Methods in Enzymology, 183, 63–99, 1990; Pearson W R and Lipman D J, Proc Nat Acad Sci USA, 85, 2444–2448,1988, available as part of the Wisconsin Sequence Analysis Package).

Preferably, the BLOSUM62 amino acid substitution matrix (Henikoff S and Henikoff J G, Proc. Nat. Acad Sci. USA, 89, 10915–10919, 1992) is used in polypeptide sequence comparisons including where nucleotide sequences are first translated into amino acid sequences before comparison.

Preferably, the program BESTFIT is used to determine the % identity of a query polynucleotide or a polypeptide sequence with respect to a reference polynucleotide or a polypeptide sequence, the query and the reference sequence being optimally aligned and the parameters of the program set at the default value, as hereinbefore described.

"Identity Index" is a measure of sequence relatedness which may be used to compare a candidate sequence (polynucleotide or polypeptide) and a reference sequence. Thus, for instance, a candidate polynucleotide sequence having, for example, an Identity Index of 0.95 compared to a reference polynucleotide sequence is identical to the reference sequence except that the candidate polynucleotide sequence may include on average up to five differences per each 100 nucleotides of the reference sequence. Such differences are selected from the group consisting of at least one nucleotide deletion, substitution, including transition and transversion, or insertion. These differences may occur at the 5' or 3' terminal positions of the reference polynucleotide sequence or anywhere between these terminal positions, interspersed either individually among the nucleotides in the reference sequence or in one or more contiguous groups within the reference sequence. In other words, to obtain a polynucleotide sequence having an Identity Index of 0.95 compared to a reference polynucleotide sequence, an average of up to 5 in every 100 of the nucleotides of the in the reference sequence may be deleted, substituted or inserted, or any combination thereof, as hereinbefore described. The same applies mutatis mutandis for other values of the Identity Index, for instance 0.96, 0.97, 0.98 and 0.99.

Similarly, for a polypeptide, a candidate polypeptide sequence having, for example, an Identity Index of 0.95 compared to a reference polypeptide sequence is identical to the reference sequence except that the polypeptide sequence may include an average of up to five differences per each 100 amino acids of the reference sequence. Such differences are selected from the group consisting of at least one amino acid deletion, substitution, including conservative and non-conservative substitution, or insertion. These differences may occur at the amino- or carboxy-terminal positions of the reference polypeptide sequence or anywhere between these terminal positions, interspersed either individually among the amino acids in the reference sequence or in one or more contiguous groups within the reference sequence. In other words, to obtain a polypeptide sequence having an Identity Index of 0.95 compared to a reference polypeptide sequence, an average of up to 5 in every 100 of the amino acids in the reference sequence may be deleted, substituted or inserted, or any combination thereof, as hereinbefore described. The same applies mutatis mutandis for other values of the Identity Index, for instance 0.96, 0.97, 0.98 and 0.99.

The relationship between the number of nucleotide or amino acid differences and the Identity Index may be expressed in the following equation:

$$n_a \leq x_a - (x_a \cdot I),$$

in which:
 $n_a$ is the number of nucleotide or amino acid differences,
 $x_a$ is the total number of nucleotides or amino acids in SEQ ID NO:1 or SEQ ID NO:2, respectively,
 I is the Identity Index,
 · is the symbol for the multiplication operator, and
in which any non-integer product of $x_a$ and I is rounded down to the nearest integer prior to subtracting it from $x_a$.

"Homolog" is a generic term used in the art to indicate a polynucleotide or polypeptide sequence possessing a high degree of sequence relatedness to a reference sequence. Such relatedness may be quantified by determining the degree of identity and/or similarity between the two sequences as hereinbefore defined. Falling within this generic term are the terms "ortholog", and "paralog". "Ortholog" refers to a polynucleotide or polypeptide that is the functional equivalent of the polynucleotide or polypeptide in another species. "Paralog" refers to a polynucleotide or polypeptide that within the same species which is functionally similar.

"Fusion protein" refers to a protein encoded by two, often unrelated, fused genes or fragments thereof. In one example, EP-A-0 464 533-A discloses fusion proteins comprising various portions of constant region of immunoglobulin molecules together with another human protein or part thereof. In many cases, employing an immunoglobulin Fc region as a part of a fusion protein is advantageous for use in therapy and diagnosis resulting in, for example, improved pharmacokinetic properties [see, e.g., EP-A 0232 262]. On the other hand, for some uses it would be desirable to be able to delete the Fc part after the fusion protein has been expressed, detected and purified.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

SEQUENCE INFORMATION

SEQ ID NO:1

ATGGTGCGATGCGACCGCGGGCTGCAGATGCTGCTGACCACGGCCGGAGCCTTCGCCGCC

TTCTCGCTCATGGCCATCGCCATCGGCACCGACTACTGGCTGTACTCCAGCGCGCACATC

TGCAACGGCACCAACCTGACCATGGACGACGGGCCCCCGCCCCGCCGCGCCCGCGGCGAC

CTCACCCACTCTGGTCTGTGGCGGGTGTGCTGCATCGAAGGGATCTATAAAGGGCACTGC

TTCCGGATCAATCACTTCCCAGAGGACAATGACTACGACCACGACAGCTCGGAGTACCTC

CTCCGCATCGTGCGAGCCTCCAGCGTCTTCCCCATCCTCAGCACCATCCTGCTCCTGCTG

GGTGGCCTGTGCATCGGTGCTGGCAGGATCTACAGCCGCAAGAACAACATCGTCCTCAGT

GCCGGCATCCTCTTCGTGGCTGCAGGCCTCAGTAACATCATCGGTATCATCGTCTACATT

TCCAGCAACACAGGTGACCCGAGTGACAAGCGGGACGAAGACAAAAAGAACCATTACAAC

TACGGCTGGTCTTTTTACTTTGGAGCTCTGTCTTTCATTGTGGCTGAGACCGTGGGCGTC

CTGGCTGTAAACATTTACATTGAGAAAAATAAAGAGTTGAGGTTTAAGACCAAACGGGAA

TTCCTTAAGGCGTCTTCCTCTTCTCCTTATGCCAGGATGCCGAGCTACAGGTACCGGCGA

CGGCGCTCGAGGTCCAGCTCAAGGTCCACCGAGGCCTCGCCCTCCAGGGACGTGTCGCCC

ATGGGCCTGAAGATCACAGGGGCCATCCCCATGGGGGAGCTGTCCATGTACACGCTGTCC

AGGGAGCCCCTCAAGGTGACCACCGCAGCCAGCTACAGCCCCGACCAGGAGGCCAGCTTC

CTGCAGGTGCATGACTTTTTCCAGCAGGACCTGAAGGAAGGTTTCCACGTCAGCATGCTG

AACCGACGGACGACCCCTGTGTGA

SEQ ID NO:2

MVRCDRGLQMLLTTAGAFAAFSLMAIAIGTDYWLYSSAHICNGTNLTMDDGPPPRRARGD

LTHSGLWRVCCIEGIYKGHCFRINHFPEDNDYDHDSSEYLLRIVRASSVFPILSTILLLL

GGLCIGAGRIYSR##IVLSAGILFVAAGLSNIIGIIVYISSNTGDPSDKRDEDKKNHYN

YGWSFYFGALSFIVAETVGVLAVNIYIEKNKELRFKTKREFLKASSSSPYARMPSYRYRR

RRSRSSSRSTEASPSRDVSPMGLKITGAIPMGELSMYTLSREPLKVTTAASYSPDQEASF

LQVHDFFQQDLKEGFHVSMLNRRTTPV

-continued

SEQUENCE INFORMATION

SEQ ID NO:3

GGATCTATAAAGGGCACTGCTTCCGGATCAATCACTTCCCAGAGGACAATGACTACGACC

ACGACAGCTCGGAGTACCTCCTCCGCATCGTGCGAGCCTCCAGCGTCTTCCCCATCCTCA

GCACCATCCTGCTCCTGCTGGGTGGCCTGTGCATCGGTGCTGGCAGGATCTACAGCCGCA

AGAACAACATCGTCCTCAGTGCCGGCATCCTCTTCGTGGCTGCAGGCCTCAGTAACATCA

TCGGTATCATCGTCTACATTTCCAGCAACACAGGTGACCCGAGTGACAAGCGGGACGAAG

ACAAAAAGAACCATTACAACTACGGCTGGTCTTTTTACTTTGGAGCTCTGTCTTTCATTG

TGGCTGAGACCGTGGGCGTCCTGGCTGTAAACATTTACATTGAGAAAAATAAAGAGTTGA

GGTTTAAGACCAAACGGGAATTCCTTAAGGCGTCTTCCTCTTCTCCTTATGCCAGGATGC

CGAGCTACAGGTACCGGCGACGGCGCTCGAGGTCCAGCTCAAGGTCCACCGAGGCCTCGC

CCTCCAGGGACGTGTCGCCCATGGGCCTGAAGATCACAGGGGCCATCCCCATGGGGAGC

TGTCCATGTACACGCTGTCCAGGGAGCCCCTCAAGGTGACCACCGCAGCCAGCTACAGCC

CCGACCAGGAGGCCAGCTTCCTGCAGGTGCATGACTTTTTCCAGCAGGACCTGAAGGAAG

GTTTCCACGTCAGCATGCTGAACCGACGGACGACCCCTGTGTGA

SEQ ID NO:4

IYKGHCFRINHFPEDNDYDHDSSEYLLRIVRASSVFPILSTILLLLGGLCIGAGRIYSRK

NNIVLSAGILFVAAGLSNIIGIIVYISSNTGDPSDKRDEDKKNHYNYGWSFYFGALSFIV

AETVGVLAVNIYIEKNKELRFKTKREFLKASSSSPYARMPSYRYRRRRSRSSSRSTEASP

SRDVSPMGLKITGAIPMGELSMYTLSREPLKVTTAASYSPDQEASFLQVHDFFQQDLKEG

FHVSMLNRRTTPV

---

What is claimed is:

1. An isolated polynucleotide comprising a nucleotide sequence encoding the polypeptide of SEQ ID NO:2.
2. The isolated polynucleotide of claim 1 which is DNA.
3. The isolated polynucleotide of claim 1 which is RNA.
4. An isolated polynucleotide comprising the polynucleotide sequence set forth in SEQ ID NO:1.
5. The isolated polynucleotide of claim 4 consisting of the polynucleotide sequence of SEQ ID NO:1.
6. An isolated polynucleotide which is fully complementary
   (a) a nucleotide sequence encoding the polypeptide of SEQ ID NO:2;
   (b) a nucleotide sequence comprising the polynucleotide sequence of SEQ ID NO:1; or
   (c) a nucleotide sequence consisting of the polynucleotide sequence of SEQ ID NO:1.
7. An expression vector comprising a polynucleotide, wherein said expression vector is capable of producing a polypeptide comprising the amino acid sequence of SEQ ID NO:2 when said expression vector is present in a compatible host cell.
8. A process for producing a recombinant host cell which comprises the step of introducing an expression vector comprising a polynucleotide capable of producing a polypeptide comprising the amino acid sequence of SEQ ID NO:2 into a cell such that the host cell, under appropriate culture conditions, produces said polypeptide.
9. A recombinant host cell produced by the process of claim 8.

* * * * *

SEQUENCE LISTING

<160> NUMBER OF SEQ ID NOS: 4

<210> SEQ ID NO 1
<211> LENGTH: 984
<212> TYPE: DNA
<213> ORGANISM: HOMO SAPIENS

<400> SEQUENCE: 1

```
atggtgcgat gcgaccgcgg gctgcagatg ctgctgacca cggccggagc cttcgccgcc      60
ttctcgctca tggccatcgc catcggcacc gactactggc tgtactccag cgcgcacatc     120
tgcaacggca ccaacctgac catggacgac gggcccccgc ccgccgcgc ccgcggcgac      180
ctcacccact ctggtctgtg gcgggtgtgc tgcatcgaag ggatctataa agggcactgc     240
ttccggatca atcacttccc agaggacaat gactacgacc acgacagctc ggagtacctc     300
ctccgcatcg tgcgagcctc cagcgtcttc cccatcctca gcaccatcct gctcctgctg     360
ggtggcctgt gcatcggtgc tggcaggatc tacagccgca agaacaacat cgtcctcagt     420
gccggcatcc tcttcgtggc tgcaggcctc agtaacatca tcggtatcat cgtctacatt     480
tccagcaaca caggtgaccc gagtgacaag cgggacgaag acaaaaagaa ccattacaac     540
```

```
tacggctggt cttttttactt tggagctctg tctttcattg tggctgagac cgtgggcgtc    600
ctggctgtaa acatttacat tgagaaaaat aaagagttga ggtttaagac caaacgggaa    660
ttccttaagg cgtcttcctc ttctccttat gccaggatgc cgagctacag gtaccggcga    720
cggcgctcga ggtccagctc aaggtccacc gaggcctcgc cctccaggga cgtgtcgccc    780
atgggcctga agatcacagg ggccatcccc atggggagc  tgtccatgta cacgctgtcc    840
agggagcccc tcaaggtgac caccgcagcc agctacagcc ccgaccagga ggccagcttc    900
ctgcaggtgc atgactttt ccagcaggac ctgaaggaag gtttccacgt cagcatgctg    960
aaccgacgga cgacccctgt gtga                                          984
```

<210> SEQ ID NO 2
<211> LENGTH: 327
<212> TYPE: PRT
<213> ORGANISM: HOMO SAPIENS

<400> SEQUENCE: 2

```
Met Val Arg Cys Asp Arg Gly Leu Gln Met Leu Leu Thr Thr Ala Gly
 1               5                  10                  15

Ala Phe Ala Ala Phe Ser Leu Met Ala Ile Ala Ile Gly Thr Asp Tyr
             20                  25                  30

Trp Leu Tyr Ser Ser Ala His Ile Cys Asn Gly Thr Asn Leu Thr Met
         35                  40                  45

Asp Asp Gly Pro Pro Arg Arg Ala Arg Gly Asp Leu Thr His Ser
 50                  55                  60

Gly Leu Trp Arg Val Cys Cys Ile Glu Gly Ile Tyr Lys Gly His Cys
 65                  70                  75                  80

Phe Arg Ile Asn His Phe Pro Glu Asp Asn Asp Tyr Asp His Asp Ser
                 85                  90                  95

Ser Glu Tyr Leu Leu Arg Ile Val Arg Ala Ser Ser Val Phe Pro Ile
            100                 105                 110

Leu Ser Thr Ile Leu Leu Leu Gly Gly Leu Cys Ile Gly Ala Gly
            115                 120                 125

Arg Ile Tyr Ser Arg Lys Asn Asn Ile Val Leu Ser Ala Gly Ile Leu
        130                 135                 140

Phe Val Ala Ala Gly Leu Ser Asn Ile Ile Gly Ile Ile Val Tyr Ile
145                 150                 155                 160

Ser Ser Asn Thr Gly Asp Pro Ser Asp Lys Arg Asp Glu Asp Lys Lys
                165                 170                 175

Asn His Tyr Asn Tyr Gly Trp Ser Phe Tyr Phe Gly Ala Leu Ser Phe
            180                 185                 190

Ile Val Ala Glu Thr Val Gly Val Leu Ala Val Asn Ile Tyr Ile Glu
        195                 200                 205

Lys Asn Lys Glu Leu Arg Phe Lys Thr Lys Arg Glu Phe Leu Lys Ala
    210                 215                 220

Ser Ser Ser Pro Tyr Ala Arg Met Pro Ser Tyr Arg Tyr Arg Arg
225                 230                 235                 240

Arg Arg Ser Arg Ser Ser Arg Ser Thr Glu Ala Ser Pro Ser Arg
                245                 250                 255

Asp Val Ser Pro Met Gly Leu Lys Ile Thr Gly Ala Ile Pro Met Gly
            260                 265                 270

Glu Leu Ser Met Tyr Thr Leu Ser Arg Glu Pro Leu Lys Val Thr Thr
        275                 280                 285

Ala Ala Ser Tyr Ser Pro Asp Gln Glu Ala Ser Phe Leu Gln Val His
```

```
                    290                 295                 300
Asp Phe Phe Gln Gln Asp Leu Lys Glu Gly Phe His Val Ser Met Leu
305                 310                 315                 320

Asn Arg Arg Thr Thr Pro Val
                325
```

<210> SEQ ID NO 3
<211> LENGTH: 764
<212> TYPE: DNA
<213> ORGANISM: HOMO SAPIENS

<400> SEQUENCE: 3

```
ggatctataa agggcactgc ttccggatca atcacttccc agaggacaat gactacgacc     60
acgacagctc ggagtacctc ctccgcatcg tgcgagcctc cagcgtcttc cccatcctca    120
gcaccatcct gctcctgctg gtggcctgt gcatcggtgc tggcaggatc tacagccgca    180
agaacaacat cgtcctcagt gccggcatcc tcttcgtggc tgcaggcctc agtaacatca    240
tcggtatcat cgtctacatt tccagcaaca caggtgaccc gagtgacaag cgggacgaag    300
acaaaaagaa ccattacaac tacggctggt cttttttactt tggagctctg tctttcattg    360
tggctgagac cgtgggcgtc ctggctgtaa acatttacat tgagaaaaat aaagagttga    420
ggtttaagac caaacgggaa ttccttaagg cgtcttcctc ttctccttat gccaggatgc    480
cgagctacag gtaccggcga cggcgctcga ggtccagctc aaggtccacc gaggcctcgc    540
cctccaggga cgtgtcgccc atgggcctga agatcacagg ggccatcccc atgggggagc    600
tgtccatgta cacgctgtcc agggagcccc tcaaggtgac caccgcagcc agctacagcc    660
ccgaccagga ggccagcttc ctgcaggtgc atgactttt ccagcaggac ctgaaggaag    720
gtttccacgt cagcatgctg aaccgacgga cgacccctgt gtga                     764
```

<210> SEQ ID NO 4
<211> LENGTH: 253
<212> TYPE: PRT
<213> ORGANISM: HOMO SAPIENS

<400> SEQUENCE: 4

```
Ile Tyr Lys Gly His Cys Phe Arg Ile Asn His Phe Pro Glu Asp Asn
1               5                  10                  15

Asp Tyr Asp His Asp Ser Ser Glu Tyr Leu Leu Arg Ile Val Arg Ala
                20                  25                  30

Ser Ser Val Phe Pro Ile Leu Ser Thr Ile Leu Leu Leu Gly Gly
            35                  40                  45

Leu Cys Ile Gly Ala Gly Arg Ile Tyr Ser Arg Lys Asn Asn Ile Val
 50                  55                  60

Leu Ser Ala Gly Ile Leu Phe Val Ala Ala Gly Leu Ser Asn Ile Ile
 65                  70                  75                  80

Gly Ile Ile Val Tyr Ile Ser Ser Asn Thr Gly Asp Pro Ser Asp Lys
                85                  90                  95

Arg Asp Glu Asp Lys Lys Asn His Tyr Asn Tyr Gly Trp Ser Phe Tyr
            100                 105                 110

Phe Gly Ala Leu Ser Phe Ile Val Ala Glu Thr Val Gly Val Leu Ala
        115                 120                 125

Val Asn Ile Tyr Ile Glu Lys Asn Lys Glu Leu Arg Phe Lys Thr Lys
    130                 135                 140

Arg Glu Phe Leu Lys Ala Ser Ser Ser Pro Tyr Ala Arg Met Pro
145                 150                 155                 160
```

-continued

```
Ser Tyr Arg Tyr Arg Arg Arg Ser Arg Ser Ser Ser Arg Ser Thr
            165                 170                 175

Glu Ala Ser Pro Ser Arg Asp Val Ser Pro Met Gly Leu Lys Ile Thr
            180                 185                 190

Gly Ala Ile Pro Met Gly Glu Leu Ser Met Tyr Thr Leu Ser Arg Glu
            195                 200                 205

Pro Leu Lys Val Thr Thr Ala Ala Ser Tyr Ser Pro Asp Gln Glu Ala
        210             215                 220

Ser Phe Leu Gln Val His Asp Phe Phe Gln Gln Asp Leu Lys Glu Gly
225                 230                 235                 240

Phe His Val Ser Met Leu Asn Arg Arg Thr Thr Pro Val
                245                 250
```